United States Patent

Ikekawa et al.

Patent Number: 5,616,609
Date of Patent: Apr. 1, 1997

[54] CARCINOSTATIC COMPOUND AND PRODUCTION THEREOF

[76] Inventors: Tetsuro Ikekawa, 5-22, Asahi-machi 1-chome, Kanazawa-shi, Ishikawa 920; Nobuo Ikekawa, 2-21-5, Kichijojihigashimachi, Musashino-shi, Tokyo 180, both of Japan

[21] Appl. No.: 185,964

[22] PCT Filed: Aug. 7, 1992

[86] PCT No.: PCT/JP92/01017

§ 371 Date: Feb. 8, 1994

§ 102(e) Date: Feb. 8, 1994

[87] PCT Pub. No.: WO93/03039

PCT Pub. Date: Feb. 18, 1993

[30] Foreign Application Priority Data

Aug. 8, 1991 [JP] Japan .................................. 3-285390

[51] Int. Cl.$^6$ ............................................. A61K 31/335
[52] U.S. Cl. .................... 514/450; 514/462; 549/330; 549/341; 549/354
[58] Field of Search .................................. 549/330, 341, 549/354; 514/450, 462

[56] References Cited

PUBLICATIONS

Feng, W. "Studies on antitumor active compounds of stellera chamaejaisme L. and their mechanism of action" CA 117:184357 (1992).

Feng, W. et al "Studies on antitumor chinese medicines, (II) Antitumor constituents of stellera charmaejasime L." CA 116:207421 (1991).

Primary Examiner—Amelia Owens
Attorney, Agent, or Firm—Oblon, Spivak, McClelland, Maier & Neustadt, P.C.

[57] ABSTRACT

Described are stelleramacrin A and stelleramacrin B represented by the following formulas (I) and (II), respectively:

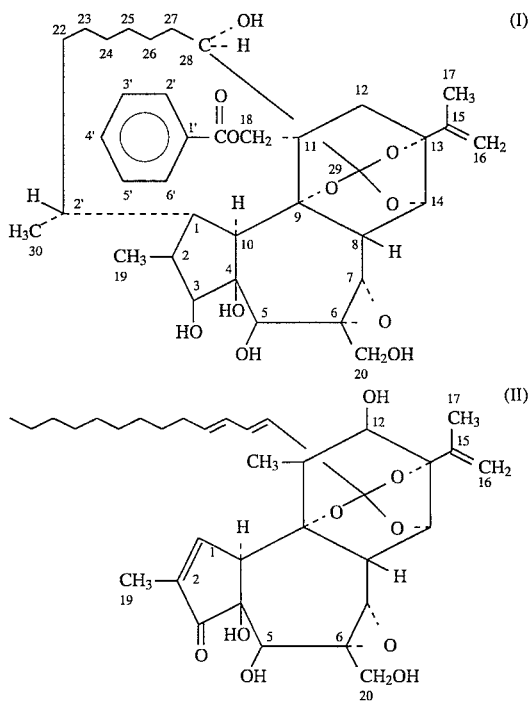

a process for the preparation thereof; and anticancer agents containing either of them as an active ingredient.

Therapeutics for solid cancer, said therapeutics containing either of gnidimacrin or pimelea factor $P_2$ as an active ingredient, are also described.

8 Claims, 2 Drawing Sheets

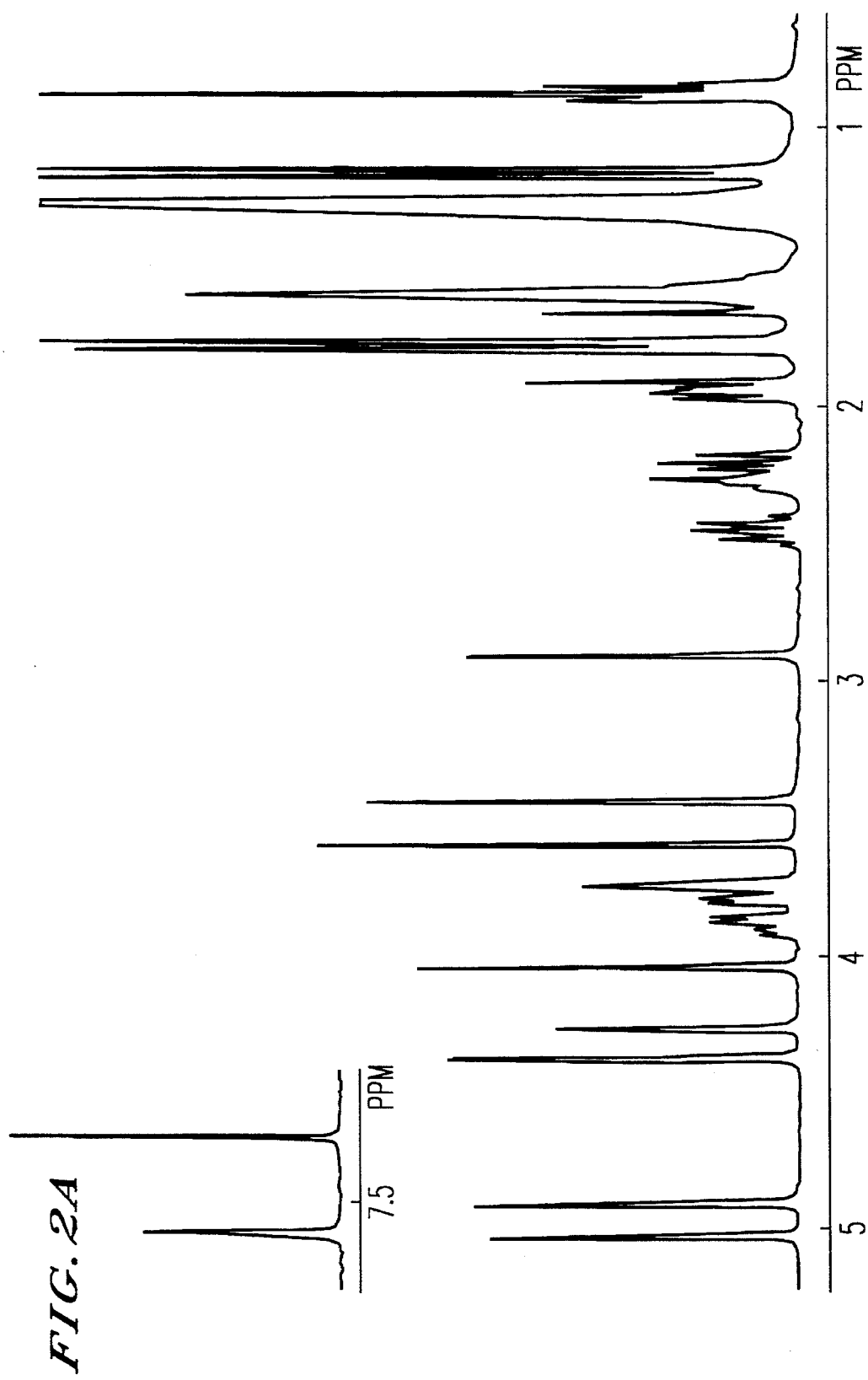

CARCINOSTATIC COMPOUND AND PRODUCTION THEREOF

This application is a 371 of PCT/JP92/01017 filed Aug. 7, 1992.

TECHNICAL FIELD

The present invention relates to anticancer compounds and a preparation process thereof, and more specifically to novel anticancer compounds contained in Rui-xiang-lang-du, that is, a Chinese herbal and crude drug, and a preparation process thereof.

BACKGROUND ART

Chinese herbal and crude drugs can be stated as the fruit of long-established wisdom of human beings. Confirming the existence of strong carcinostatic activities in Rui-xiang-lang-du (*Stellera chamaejasme. L, Euphorbia fischeriana Steud., E. ebiacteola Hayata*) in the course of a study on carcinostatic Chinese herbal and crude drugs, the essences of whose carcinostatic activities have not yet been identified, the present inventors filed a patent application on a process for the collection of its carcinostatic substance (Japanese Patent Application No. 58126/1990). The application, however, did not deal to such an extent as efficiently isolating a compound having carcinostatic activities and confirming its effectiveness against solid cancer.

DISCLOSURE OF THE INVENTION

The present inventors have proceeded with further research on a carcinostatically active component contained in the carcinostatic substance of Rui-xiang-lang-du, resulting in successful isolation of a component contributing to the carcinostatic activities of Rui-xiang-lang-du. In addition, the component has also been found to contain a novel compound represented by the formula described below.

Namely, a first object of the present invention is to provide stelleramacrin A and stelleramacrin B represented by the following formulas (I) and (II), respectively:

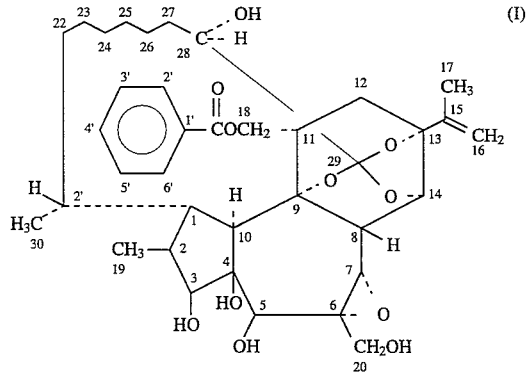

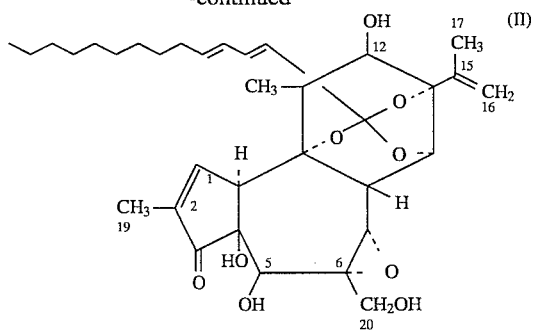

A second object of the present invention is to provide a process for the preparation of stelleramacrin A or stelleramacrin B from Rui-xiang-lang-du.

Another object of the present invention is to provide an anticancer agent containing stelleramacrin A or stelleramacrin B.

A further object of the present invention is to provide a therapeutic for solid cancer, said therapeutic containing gnidimacrin or pimelea factor $P_2$ as an active ingredient.

BRIEF DESCRIPTION OF THE DRAWINGS

FIG. 2 is a proton NMR spectrum of stelleramacrin

BEST MODES FOR CARRYING OUT THE INVENTION

Figure 1:
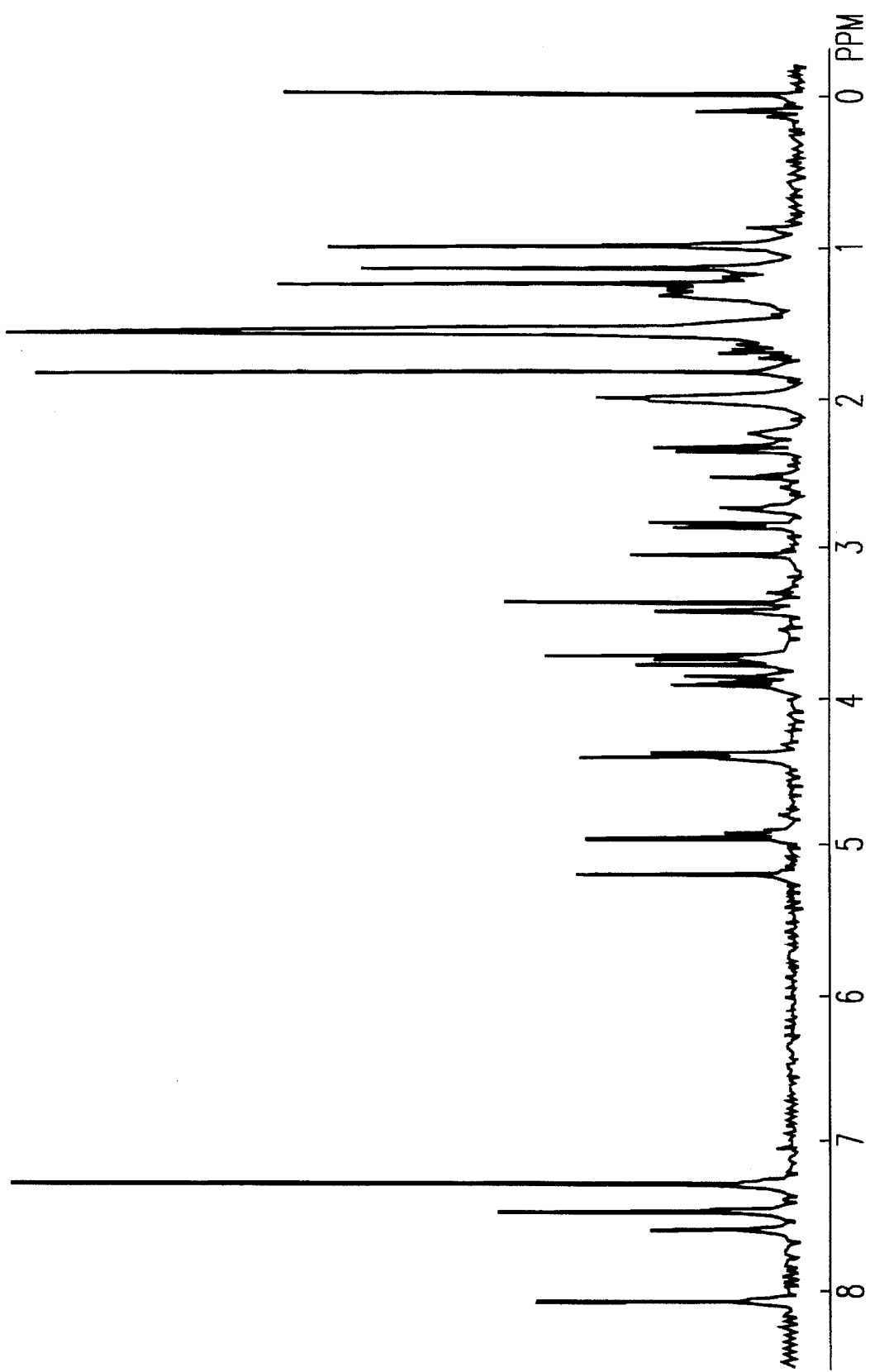
FIG. 1 is a proton NMR spectrum of stelleramacrin A according to the present invention.

Stelleramacrin A and stelleramacrin B (which may hereinafter be collectively called "stelleramacrin") according to the present invention, which are represented by the formulas (I) and (II), respectively, can each be obtained by extracting an aerial or subterranean part (rootstock) of Rui-xiang-lang-du with an organic solvent and then purifying the extract.

Described specifically, an aerial or subterranean part of Rui-xiang-lang-du, for example, is extracted with a lower alcohol such as methanol, ethanol or propanol and the extract is then extracted with a water-insoluble organic solvent such as petroleum ether to obtain a crude extract. In the next place, the crude extract is purified by chromatography on a silica gel column while using hexane-ethyl acetate or the like as an eluent, chromatography on an ODS column while using methanol-water, or a like method, whereby some active fractions are obtained. The active fractions are subjected to high-performance liquid chromatography and preparative thin-layer chromatography for further purification, whereby stelleramacrin represented by the formula (I) or (II) can be isolated as a compound having carcinostatic activities.

Although anticancer compounds other than stelleramacrin, for example, gnidimacrin [J. Nat. Prod. 1985, 48(3), 440–445], pemelea factor $P_2$ (Abstracts of Lectures addressed at Natural Organic Compounds Forum, 27, 734–741), subtoxin A (Abstracts of Lectures addressed at Natural Organic Compounds Forum, 27, 734–741), huratoxin (Abstracts of Lectures addressed at Natural Organic Compounds Forum, 27, 734–741) and simplexin [Aust. Vet. J., 51(6), 325–326] are also contained, stelleramacrin is obtained in fractions different from those of such other anticancer compounds in the separation and purification steps according to the process described above. Its structure is determined by analyzing the same on the basis of its ultraviolet absorption spectrum, proton nucleus magnetic resonance spectrum, mass spectrum or the like.

Incidentally, gnidimacrin, pimelea factor $P_2$ and the like which are also anticancer compounds obtained from Rui-xiang-lang-du are known substances. Such known substances have long been regarded effective for the therapy of ascites-type leukemia. As can be understood easily from the therapeutic cases by carbazylquinone and bleomycin, for example, no correlation has been recognized between action against leukemia and carcinostatic activities against solid cancer. It was not known at all about whether or not these compounds have carcinostatic activities against solid cancer.

As a result of the study by the present inventors, it has been found for the first time that gnidimacrin and pimelea factor $P_2$ also have strong inhibiting action against solid cancer such as gastric cancer, pulmonary cancer, liver cancer or the like.

When stelleramacrin according to the present invention is employed as an anticancer agent or when gnidimacrin or pimelea factor $P_2$ is used as a therapeutic for solid cancer, each of these compounds can be administered to animals or men neat or in combination with one or more conventionally-employed, pharmaceutically-acceptable carriers.

No particular limitation is imposed on the administration form of stelleramacrin, gnidimacrin and pimelea factor $P_2$, so that a suitable administration form can be selected as need. These compounds may each be administered either as an oral preparation such as tablets, capsules, granules, fine subtilaes, powders or the like, or as a parenteral preparation such as injections or suppositories.

Stelleramacrin A, a novel compound prepared according to the present invention, has an $LD_{50}$ value of 5 mg/kg while stelleramacrin B, also a novel compound prepared according to the present invention, has an $LD_{50}$ value of 12 mg/kg. When these compounds are used as oral preparations, their dosage varies depending on the age, body weight and conditions of each patient. To bring about intended effects, stelleramacrin may be added. in an amount of about 0.02 mg to 20 mg a day per adult in several portions.

It is proper, on the other hand, to administer gnidimacrin or pimelea factor $P_2$ in an amount of about 0.01 to 10 mg a day per adult.

Oral preparations can be formulated in a manner known per se in the art by using, as an excipient, starch, lactose, sucrose, mannitol, caboxymethylcellulose, corn starch or an inorganic salt. For the formulation of oral preparations, one or more of binders, disintegrators, surfactants, lubricants, fluidity improvers, corrigents, colorants, perfumes and the like can also be added. Specific examples of these additives will be illustrated hereinafter.

Examples of the binder include starch, dextrin, gum arabic powder, gelatin, hydroxypropyl starch, methylcellulose, sodium carboxymethylcellulose, hydroxypropylcellulose, crystalline cellulose, ethylcellulose, polyvinyl pyrrolidone and macrogol.

Examples of the disintegrator include starch, hydroxypropyl starch, sodium carboxymethylcellulose, calcium carboxymethylcellulose, carboxymethylcellulose and low-substituted hydroxypropylcellulose.

Illustrative surfactants include sodium laurylsulfate, soybean lecithin, sucrose fatty acid esters and polysorbate 80.

Exemplary lubricants include talc, waxes, hydrogenated vegetable oils, sucrose fatty acid esters, magnesium stearate, calcium stearate, aluminum stearate and polyethylene glycol.

Examples of the fluidity improver include light silicic anhydride, dried aluminum hydroxide gel, synthetic aluminum silicate and magnesium silicate.

The compounds, which pertain to the present invention, can also be administered as suspensions, emulsions, syrups or elixirs. These preparation forms may contain a corrigent, colorant and/or the like.

When the compounds according to the present invention are employed as parenteral preparations, their dosage to bring about intended effects varies depending on the age, body weight and conditions of the patient. In general, it is necessary to administer about 0.005 mg to 5 mg a day, in terms of the weight of each compound, per adult by intravenous injection, intravenous drip infusion, subcutaneous injection or intramuscular injection.

These parenteral preparations can be formulated in a manner known per se in the art. Illustrative usable diluents include distilled water for injection, physiological saline, an aqueous glucose solution, vegetable oil for injection, sesame oil, peanut oil, soybean oil, corn oil, propylene glycol and polyethylene glycol. Sterilizers, antiseptics, stabilizers and/or the like can also be added as needed.

As a preferred method from the viewpoint of stability, it is also possible to fill such a parenteral preparation in vials, and then to freeze it to remove its water, thereby forming it into a lyophilizate by a usual lyophillization technique. Immediately before use, the lyophillizate can be reconstituted into a liquid preparation.

Isotonicities, stabilizers, antiseptics, soothing agents and/or the like can also be added as needed.

Further examples of the parenteral preparation include coating preparations such as external liquid preparations and ointments and suppositories for rectal administration. They can be formulated in a manner known per se in the art.

The present invention will hereinafter be described in further detail by the following Examples.

EXAMPLE 1

A subterranean part (1 kg) of Stellera chamejasme. L was pulverized, followed by the addition of 3 1 of methanol. The resultant mixture was heated for 5 hours under. reflux for extraction. The residue of the extraction was extracted again under the same conditions. The both extracts were combined together and then filtered under reduced pressure, whereby 153.6 g of methanol extract were obtained. The methanol extract was extracted further with petroleum ether for 5 hours in a Soxhlet extractor, whereby 15.8 g of a petroleum ether extract (MMP) were obtained.

The resultant MMP (6.5 g) was subjected to chromatography on a silica gel column (5 cm in diameter and 16.5 cm in length), followed by the successive eluation with hexane-ethyl acetate as an eluent [1:4(v/v), 1:2(v/v), 1:1(v/v)] to effect fractionation. Eluate fractions (1 g) corresponding to the 1:1 (v/v) mixed solvent of hexane and ethyl acetate were subjected to high-performance liquid chromatography on an ODS reversed phase column (0.2 cm in diameter, 25 cm in length), followed by the eluation with a 10:1 (v/v) mixed solvent of methanol and water. As a result, confirmed was the existence of substances having strong carcinostatic activities in fractions which were obtained at retention times of 9.5 min, 11.4 min, 14.8 min, 17.2 min, 19.8 min and 21.0 min, respectively. These fractions were designated as Fraction 1, Fraction 2, Fraction 3, Fraction 4, Fraction 5 and Fraction 6 in the increasing order of the retention times.

Each fraction was thereafter purified by repeating preparative thin-layer chromatography on a silica gel column [hexane:ethyl acetate=1:2 (v/v)] and preparative high-performance liquid chromatography on an ODS column [methanol:water=10:1 (v/v)] as many times as needed, whereby a single compound was isolated. The yields of the single compounds so isolated were 1.90 mg from Fraction 1, 3.29 mg from Fraction 2, 2.06 mg from Fraction 3, 8.23 mg from Fraction 4 and 1.23 mg from Fraction 5. When an aerial part of Rui-xiang-lang-du was used instead as a raw material, obtained were 1.35 mg from Fraction 1 and 3.61 mg from Fraction 2 in exactly the same manner.

As a result of determination of the chemical structure of each of the compounds so isolated, the compound isolated from Fraction 1 was found to be a novel compound represented by the formula (1). This compound was named "stelleramacrin A" by the present inventors. The compound isolated from Fraction 2 was identified as gnidimacrin, that from Fraction 3 as pimelea factor $P_2$, that from Fraction 4 as subtoxin A, that from Fraction 5 as huratoxin and that from Fraction 6 as simplexin.

Physicochemical properties of stelleramacrin, the novel compound, among the isolated compounds will be described below:

Physicochemical properties of stelleramacrin:
  Molecular formula: $C_{37}H_{50}O_{11}$
  Appearance: white powder
  Mass analysis: M+H=671
  Benzoyl group: 1
  Daphnan-system: the skeleton of diterpene is contained.

Proton nuclear magnetic resonance spectrum ($\delta$ppm in $CDCl_3$) $^1$H-NMR: 2.59(1H,dd,J=12.5), 1.65(1H,m), 3.81(1H,d), 3.72–3.95(1H), 3.39(1H,s), 3.03 (1H,d,J=2.9), 2.91(1H,d,J=12.5), 2.76(1H,m), 2.02(1H,d, J=7.5), 2.32(1H, d,J=14.7), 4.40(1H, d,J=2.9), 5.19(1H,s), 4.95(1H,s), 1.84(3H,s), 4.92(1H,bd,J=10.0), 4.37(1H,t,J=10.0), 1.17 (3H,d,J=7.6), 3.89(1H,d,J=10.0), 3.73(1H,d, J=11), 2.26(1H,m), 3.78–3.89(1H,d,J=7.3), 1.00(3H,d,J=7.6), 8.07(1H,m), 7.57 (1H,m), 7.47 (2H,m)

Carbon nuclear magnetic resonance spectrum ($\delta$ppm in $CDCl_3$) $^{13}$C-NMR: 14.58, 18.20, 19.05, 22.81, 23.11, 23.61, 24.19, 25.18, 27.25, 28.52, 29.51, 36.53, 37.62, 40.85, 48.01, 48.13, 61.28, 63.18, 65.12, 68.27, 70.81, 72.08, 78.47, 79.42, 81.03, 81.34, 84.42, 111.89, 118.50, 128.43, 129.73, 130.30, 133.13, 145.56, 167.09.

EXAMPLE 2

MMP (2 g), which had been obtained in the manner described in Example 1, was subjected to open-column chromatography (ODS column, methanol:water=10:1, v/v) employing as a carrier ODS (LC sorb, "Sp-A-ODS"; product of KEMCO CORP), followed by the elution with a 9:1 (v/v) mixed eluate of methanol and water. As a result of detection of the eluate so obtained at 254 nm, six fractions were obtained. It was confirmed that among them, Fraction 1, 2 and 3 had strong carcinostatic activities- Fraction 2, which showed the strongest carcinostatic activities, was subjected further to preparative high-performance liquid chromatography on a Shim-Pack pREP-ODS column (20 mm×25 cm), followed by the elution with a 10:1 (v/v) mixed solvent of methanol and water while monitoring fractions by UV at 228 nm. As a result, stelleramacrin A, gnidimacrin and stelleramacrin B were found to be eluted at elution times of 17.5 min, 27.9 min and 44.4 min, respectively.

Proton NMR spectra of stelleramacrin A and stelleramacrin B so obtained are shown in FIG. 1 and FIG. 2, respectively.

In addition, stelleramacrin was also obtained from Fraction 1 and Fraction 3 described above.

Test 1

The mouse leukemia cell P-388 was intraperitoneally transplanted to $BDF_1$ mice in an amount of $1\times10^6$ cells per mouse. From the following day, each test drug was intraperitoneally administered to the mice once a day for 5 days. Each test group was compared in the number of survival days with a control group to determine an apothanasia rate. The results are shown in Table 1.

TABLE 1

| Test drug | Dosage (mg/kg) | Average number of survival days (days) | Apothanasia rate (%) |
|---|---|---|---|
| Control group | | 8.08 | |
| Stelleramacrin A | 1 | 13.83 | 71 |
| Stelleramacrin B | 1 | 12.17 | 48 |

Test 2

Cells of gastric cancer, pulmonary cancer, liver cancer and leukemia, which had been separated from human patients, were separately placed in portions of RMP-1640 medium containing 10% calf serum and then incubated at 37° C. for 4 days in a 5% $CO_2$-incubator to obtain a cell population of $10^4$/ml. To the cells of each cancer kind so cultured, stelleramacrin was added at varied concentrations, and the concentration ($IC_{50}$) of each test compound at which proliferation of the human cancer cells was inhibited by 50% was determined. The results are shown in Table 2.

TABLE 2

| Site of cancer | Kind of cancer | $IC_{50}$ (μg/ml) | |
|---|---|---|---|
| | | Stelleramacrin A | Stelleramacrin B |
| Gastric cancer | MKU-28 | 0.2 | 1 |
| | MKV-74 | >10 | >10 |
| | K-III | 0.1 | 1.5 |
| | MKV-45 | 0.8 | 2.7 |
| Pulmonary cancer | LU-99 | >10 | >10 |
| | N-237 | 5.3 | >10 |
| | H-69 | 10.2 | >10 |
| | PC-14 | 8.4 | >10 |
| | PC-7 | 5.1 | 7.3 |
| Liver cancer | HLE | >10 | >10 |
| Leukemia | K-502 | 10 | >10 |

Test 3

Hypodermically transplanted to induce solid cancer were Lewis pulmonary cancer cells to $BDF_1$ mice in an amount of $1\times10^6$ cells per mouse, Clon 26 large bowel cancer cells to BALB/C mice in an amount of $5\times10^5$ cells per mouse and a 20% homogenate of B-16 melanoma solid cancer to $BDF_1$ mice in an amount of 0.25 ml per mouse. From the following day of the transplantation, gnidimacrin and pimelea factor $P_2$ were administered separately once a day for 5 days. Each test group was compared in apothanasia rate with a control group. The results on gnidimacrin and pimelea factor $P_2$ are shown in Table 3 and Table 4, respectively.

TABLE 3

| Kind of cancer | Dosage (mg/kg) | Apothanasia rate (%) |
| --- | --- | --- |
| Lewis pulmonary cancer | 0.02 | 40.0 |
| B-16 melanoma | 0.02 | 49.2 |
| Colon 26 large bowel cancer | 0.01 | 26.8 |

TABLE 4

| Kind of cancer | Dosage (mg/kg) | Apothanasia rate (%) |
| --- | --- | --- |
| Lewis pulmonary cancer | 0.1 | 35.2 |
| B-16 melanoma | 0.1 | 41.8 |
| Colon 26 large bowel cancer | 0.05 | 18.5 |

In addition, gnidimacrin showed an apothanasia rate of 47.8% when administered intravenously to mice which had been transplanted With Lewis pulmonary cancer cells in an amount of 0.06 mg/Kg.

Test 4

Cells of gastric cancer, pulmonary cancer, liver cancer and leukemia, which had been separated from human patients, were separately placed on portions of RMP-1640 medium containing 10% calf serum and then incubated at 37° C. for 4 days in a 5% $CO_2$-incubator to obtain a cell population of $10^4$/ml. To the cells of each cancer kind so cultured, gnidimacrin or pimelea factor was added at varied concentrations, and the concentration ($IC_{50}$) of the test compound at which proliferation of the human cancer cells was inhibited by 50% was determined. The results are shown in Table 5.

TABLE 5

| Site of cancer | Kind of cancer | $IC_{50}$ (μg/ml) Gnidimacrin | Pimelea factor |
| --- | --- | --- | --- |
| Gastric cancer | MKU-28 | 0.006 | 0.01 |
|  | MKV-74 | >1 | 10 |
|  | K-III | 0.0006 | 0.003 |
|  | MKV-45 | 0.0001 | 0.005 |
| Pulmonary cancer | LU-99 | 1 | 10 |
|  | N-237 | 0.2 | 3.8 |
|  | H-69 | 0.6 | 7 |
|  | PC-14 | 0.85 | 3.2 |
|  | PC-7 | 0.5 | 1.7 |
| Liver cancer | HLE | 2 | 10 |
| Leukemia | K-502 | 0.0025 | 0.3 |

Test 5

Using laboratory animals, effects of gnidimacrin on solid cancer were studied. First, intradermally inoculated to male BALB/c mice (each group consisting of 6 mice, each having a weight of 17–21 g) was 0.01 ml of RPMI 1640 solution which contained 10% fetal serum and $1 \times 10^5$ cells/ml of Meth A fibrosarcoma. Seven days after the inoculation, solid cancer was formed. Into the solid cancer, gnidimacrin which had been dissolved in physiological saline containing 0.5% CMC, was administered at 0.001 mg/Kg by injection. That administration was conducted once a day for 5 days. On the 21st day from the inoculation of Meth A fibrosarcoma, the cancer was cut out and its weight was compared with that of a control group not administered with gnidimacrin. As a result, it was found that the average cancer weight was 0.4 g for the gnidimacrin-administered group but 2.1 g for the control group. Namely, gnidimacrin inhibited the proliferation of the solid cancer by 81%.

Preparation Example 1

| Tablets (Formulation) | |
| --- | --- |
| (1) Corn Starch | 48 g |
| (2) Crystalline cellulose | 42 g |
| (3) Calcium carboxymethylcellulose | 8 g |
| (4) Light silicic acid anhydride | 0.5 g |
| (5) Magnesium stearate | 0.5 g |
| (6) Stelleramacrin A | 1 g |
| Total | 100 g |

(Procedures)

The above ingredients (1)–(6) were mixed uniformly according to the above formulation and then compressed into tablets, of 200 mg each, by a tableting machine.

Each tablet so obtained contains 2 mg of stelleramacrin A obtained in Example 1. Per adult, 1–10 tablets are administered a day in several portions.

Preparation Example 2

| Granules (Formulation) | |
| --- | --- |
| (1) Corn starch | 88 g |
| (2) Magnesium stearate | 1.5 g |
| (3) Calcium carboxymethylcellulose | 8 g |
| (5) Light silicic acid anhydride | 1.5 g |
| (6) Stelleramacrin B | 1 g |
| Total | 100 g |

(Procedures)

The above ingredients (1)–(5) were mixed uniformly according to the above formulation and then compression-molded by a compression molding machine, followed by the crushing by a pulverizer and shifting into granules.

The resultant granules contain stelleramacrin B, which had been obtained in Example 2, in an amount of 10 mg/g. Per adult, 0.1–2 g of the granules are administered a day in several portions.

Preparation Example 3

| Capsules: (Formulation) | |
| --- | --- |
| (1) Corn starch | 98.5 g |
| (2) Light silicic acid anhydride | 1.0 g |
| (3) Stelleramacrin A | 0.5 g |
| Total | 100 g |

(Procedures)

The above ingredients (1)–(3) were mixed uniformly according to the above formulation and No. 2 capsules were each filled with 200 mg of the resulting mixture.

Each capsule contains 1 mg of stelleramacrin A, which had been obtained in Example 1. Per adult, 1 to 20 capsules are administered a day in several portions.

Preparation Example 4

| Injection: (Composition) | |
|---|---|
| (1) Distilled water for injection | 89.5 g |
| (2) Soybean oil | 5 g |
| (3) Soybean phosphatide | 2.5 g |
| (4) Glycerin | 2 g |
| (5) Stelleramacrin A | 1 g |
| Total | 100 g |

(Procedures)

The ingredient (5) was dissolved in a mixture of the ingredients (2) and (3). To the resulting solution, the ingredients (1) and (4) were added, followed by emulsification, whereby an injection was obtained.

Industrial Applicability

As has been described above, stelleramacrin according to the present invention has high carcinostatic activities and can hence be employed as an anticancer agent applicable to a wide variety of cancer.

In addition, gnidimacrin- or pimelea-factor-$P_2$-containing therapeutics for solid cancer are useful for the treatment of solid cancer such as gastric cancer, pulmonary cancer, liver cancer, mammary cancer and the like.

We claim:

1. Purified stelleramacrin A or purified stelleramacrin B represented respectively by the following formulas (I) and (II):

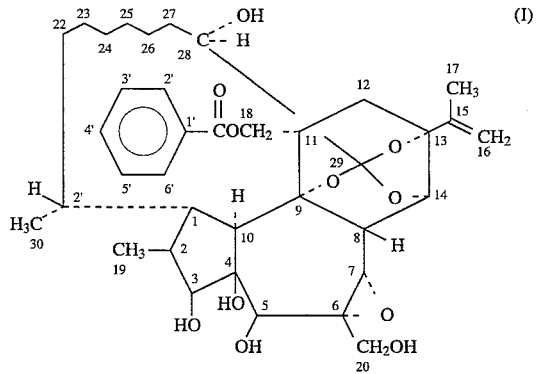

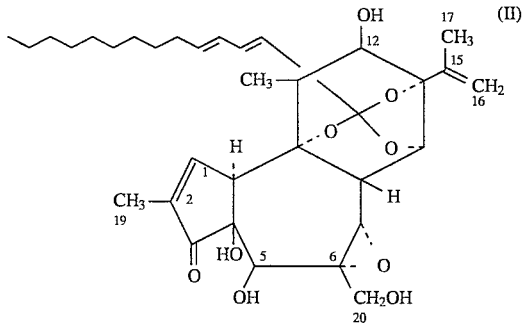

2. A process for the preparation of stelleramacrin A or stelleramacrin B, which comprises extracting a subterranean or aerial part of Rui-xiang-lang-du with a lower alcohol, extracting the extract with a water-insoluble organic solvent, isolating a stelleramacrin-A-containing fraction or a stelleramacrin-B-containing fraction from the resulting extract, and then purifying the isolated fraction.

3. An anticancer agent comprising purified stelleramacrin A or purified stelleramacrin B as an active ingredient.

4. An anti-cancer agent according to claim 3 which is effective for treating gastric cancer, pulmonary cancer, liver cancer or leukemia.

5. A therapeutic agent for solid cancer, said therapeutic agent comprising an effective amount of purified gnidimacrin.

6. A therapeutic agent for solid cancer, said therapeutic agent comprising an effective amount of purified pimelea factor $P_2$.

7. A therapeutic agent according to claim 5, wherein said solid cancer is selected from gastric cancer, pulmonary cancer, liver cancer or fibrosarcoma.

8. A therapeutic agent according to claim 6, wherein said solid cancer is selected from gastric cancer, pulmonary cancer, liver cancer or fibrosarcoma.

* * * * *